United States Patent
Schäfer et al.

(10) Patent No.: US 12,376,950 B2
(45) Date of Patent: Aug. 5, 2025

(54) BRUSH HEAD, TOOTHBRUSH, ANALYSIS SYSTEM AND METHOD FOR THE OPERATION THEREOF

(71) Applicant: BIOINITIALS GMBH, Bl (CH)

(72) Inventors: Christoph Schäfer, Engelberg (CH);
Fabio Cirillo, Ormalingen (CH);
Christian Jäggi, Biel-Benken (CH);
Stefan Schaffner, Münchenstein (CH);
Stefan Stübinger, Binningen (CH);
Saso Jezernik, Regensdorf (CH)

(73) Assignee: BIOINITIALS GmbH, Biel-Benken (CH)

( * ) Notice: Subject to any disclaimer, the term of this patent is extended or adjusted under 35 U.S.C. 154(b) by 360 days.

(21) Appl. No.: 17/760,534

(22) PCT Filed: Sep. 15, 2020

(86) PCT No.: PCT/EP2020/075780
§ 371 (c)(1),
(2) Date: Mar. 15, 2022

(87) PCT Pub. No.: WO2021/052970
PCT Pub. Date: Mar. 25, 2021

(65) Prior Publication Data
US 2022/0354628 A1    Nov. 10, 2022

(30) Foreign Application Priority Data
Sep. 16, 2019    (DE) .................... 20 2019 105 110.8

(51) Int. Cl.
*A61C 19/04*    (2006.01)
*A61C 17/22*    (2006.01)

(52) U.S. Cl.
CPC ............ *A61C 19/04* (2013.01); *A61C 17/221* (2013.01)

(58) Field of Classification Search
CPC ..... A61C 19/04; A61C 17/221; A61C 17/065; A61B 5/6898; A61B 5/0022; G16H 50/20; G16H 40/67
(Continued)

(56) References Cited

U.S. PATENT DOCUMENTS

| | | |
|---|---|---|
| 6,623,698 B2 | 9/2003 | Kuo |
| 7,269,873 B2 | 9/2007 | Brewer et al. |

(Continued)

FOREIGN PATENT DOCUMENTS

| | | | |
|---|---|---|---|
| AT | A184692 A | 11/1994 | |
| AT | 399779 B | 7/1995 | |

(Continued)

OTHER PUBLICATIONS

International Search Report mailed Nov. 19, 2020 in related/corresponding International Application No. PCT/EP2020/075780.

(Continued)

*Primary Examiner* — Katina N. Henson
(74) *Attorney, Agent, or Firm* — PATENT PORTFOLIO BUILDERS PLLC

(57) ABSTRACT

A brush head of a toothbrush includes a plurality of bristles for cleaning teeth and a sensor unit for monitoring the health status of a user regarding development of paradontitis, cavities, periodontitis, and/or for health monitoring. The sensor unit is exchangeably arranged on or in the brush head.

19 Claims, 8 Drawing Sheets

(58) Field of Classification Search
USPC .................................................. 15/167.1
See application file for complete search history.

(56) References Cited

U.S. PATENT DOCUMENTS

| | | |
|---|---|---|
| 8,839,476 B2 | 9/2014 | Adachi |
| 2002/0127143 A1 | 9/2002 | Kuo |
| 2008/0060148 A1 | 3/2008 | Pinyayev et al. |
| 2012/0322023 A1* | 12/2012 | Hohlbein .......... A46B 15/0002 433/27 |
| 2014/0199651 A1* | 7/2014 | Adachi ............. A46B 15/0034 433/27 |
| 2015/0088538 A1* | 3/2015 | Dykes ................. A61C 17/065 600/300 |
| 2016/0374609 A1 | 12/2016 | Vetter et al. |
| 2018/0098620 A1* | 4/2018 | Lee ................... A61C 17/3481 |
| 2019/0053614 A1* | 2/2019 | Kawabata ............. A61C 17/22 |

FOREIGN PATENT DOCUMENTS

| | | |
|---|---|---|
| AT | A186493 A | 5/2000 |
| AT | 407199 B | 1/2001 |
| AU | 2014364786 B2 | 6/2015 |
| CA | 2605308 C | 1/2015 |
| CN | 102655788 A | 9/2012 |
| CN | 104705996 A | 6/2015 |
| CN | 106456301 A | 2/2017 |
| CN | 107928099 A | 4/2018 |
| CN | 108185632 A | 6/2018 |
| CN | 209376990 U | 9/2019 |
| DE | 102006022290 A1 | 11/2007 |
| DE | 102011085747 A1 | 5/2013 |
| DE | 112012003494 T5 | 5/2014 |
| KR | 200371450 Y1 | 1/2005 |
| KR | 101513262 B1 | 4/2015 |
| KR | 20180040060 A * | 1/2017 |

OTHER PUBLICATIONS

Search Report created Mar. 3, 2020 in related/corresponding DE Application No. 20 2019 105 110.8.
Written Opinion mailed Nov. 19, 2020 in related/corresponding International Application No. PCT/EP2020/075780.
Office Action created Jan. 12, 2024 in related/corresponding CN Application No. 202080065047.X.
Koncki et al.; "Disposable Screen-Printed pH-Electrode for Determination of Anticholinesterase Activity;" Biosensors for Direct Monitoring of Environmental Pollutants in Field; Part of the NATO ASI Series book series (ASEN2, vol. 38); 1998; pp. 139-144.
Office Action dated Sep. 8, 2023 in related/corresponding EP Application No. 20786243.4.

* cited by examiner

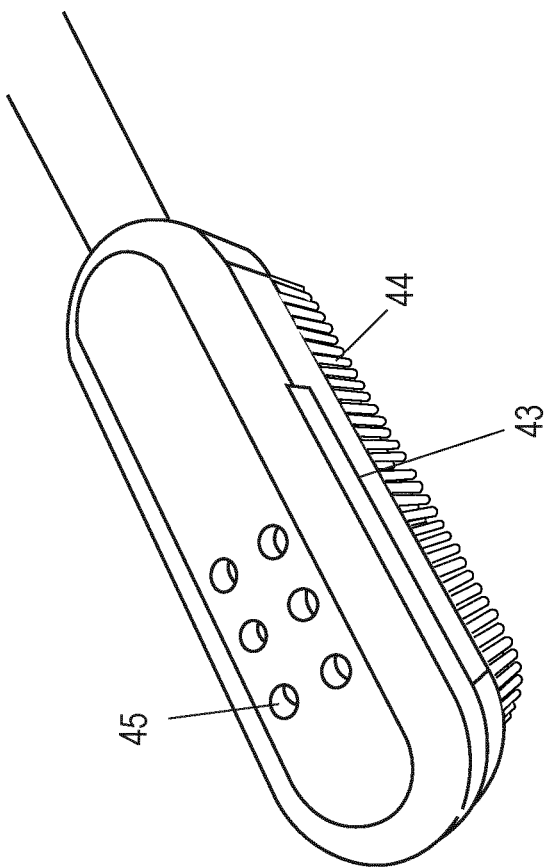
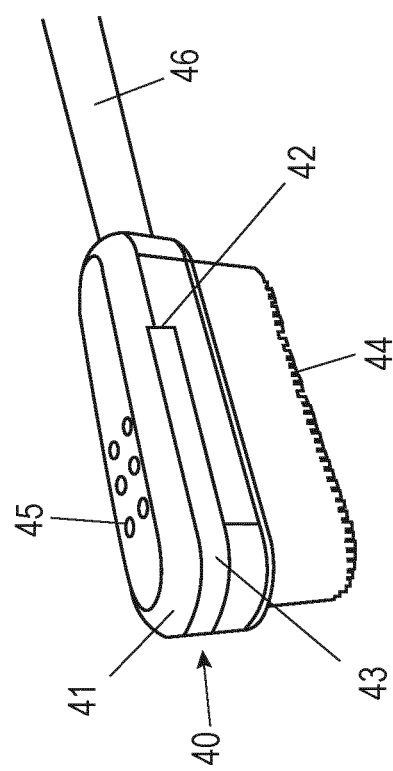

BRUSH HEAD, TOOTHBRUSH, ANALYSIS SYSTEM AND METHOD FOR THE OPERATION THEREOF

BACKGROUND AND SUMMARY OF THE INVENTION

Exemplary embodiments of the present invention relate to a brush head, a toothbrush for monitoring health status, as well as to an analysis system and a method for its operation.

U.S. Pat. No. 6,623,698 B discloses a device for detecting blood sugar, pregnancy, HIV, and the like. This toothbrush assumes one and/or more interchangeable toothbrush attachments. The attachments have integrated sensors.

The sensors are either optical sensors or electrical sensors. The publication discloses a time-sequential measurement with a first time phase in which saliva collection and measurement takes place and a subsequent second time phase in which only brushing of the teeth takes place.

Although this publication and thus also the associated technology have been known for some time, a product realized with it has not become commercially established. One possible reason could be seen in the type of sensors used in the brush. If biosensors with a short service life of several days were used in an aforementioned brush head, the replacement intervals of the brush head would be very short.

On the other hand, special attention must be paid to hygiene in dentistry. Furthermore, some sensors are no longer reliable after a short period of use, usually even once.

Based on this, exemplary embodiments of the present invention are directed to providing a toothbrush which has a brush head with an integrated and interchangeable sensor unit.

A brush head of a toothbrush according to the invention has one or more means for mechanical cleaning of the teeth. In a preferred embodiment, these are described below as a plurality of bristles for cleaning the teeth. Typically, these bristles are arranged along a front face.

However, it is also possible within the scope of the present invention that, alternatively or in addition to the bristles, one or more other means are used for mechanical cleaning of teeth. This or these means may comprise, inter alia, a sponge, a pad, one or more microfiber structures or one or more vibrating elements. Accordingly, the brush with microfiber structures is then a textile brush with textile instead of bristles, or a sponge brush with a sponge structure instead of bristles, or a vibration brush with one or more vibration elements.

The following further description is based on the preferred embodiment with the bristles, although other means as described can of course also be used.

Furthermore, the brush head has a sensor arrangement that serves to monitor the state of health of a user. In the context of the present invention, health is understood to mean both the presence and concentration of pathogens, such as viruses, fungi and/or bacteria, as well as the presence of carcinomas, cardiovascular diseases, gastric ulcers, reflux, diabetes or also the fertility state, e.g., impending ovulation, or also the pregnancy state of a user. The above list is not exhaustive, but can be supplemented by other examples.

Monitoring of the state of health can be provided, among other things, by measuring pathogens such as the concentration of bacteria, viruses, and the like, or, for example, by detecting the body's defense reactions, such as the detection of antibodies. Other measurements, such as temperature and/or conductivity, can also be used alone or in combination with other measurement data to monitor the state of health.

The monitoring of the health status can optionally and preferably be carried out based on a personalized health profile, which was created in a healthy state, e.g., a visit to the doctor. In this case, the changes in the measurements can always be compared with this health profile.

In contrast to the prior art, the sensor unit is interchangeably arranged on or in the brush head of the toothbrush. The sensor unit can be part of a sensor arrangement, which can also be designed to be interchangeable.

The brush head itself may be interchangeably arranged on the handle of a toothbrush, or it may be permanently connected to the toothbrush. Typically, the replacement period of a brush head is after more than 1 month, for example every 3-4 months, while the sensor unit or sensor assembly should preferably be replaced after each measurement or after a few measurements.

The sensor arrangement can have several different sensor units. When the sensor arrangement is replaced, several sensor units can thus be replaced at the same time. Still other sensor units can be permanently, i.e., non-interchangeably, connected to the brush head and/or the handle of the toothbrush.

The sensor unit can be located on the side of the brush head, on the back or even between the bristles, analogous to a sieve.

The use of an interchangeable disposable sensor unit and, particularly preferably, an interchangeable disposable sensor arrangement enables, for example, a single and metered delivery of an indicator, e.g., an indicator dye or biomarker, to a or the aforementioned sensor unit. The same applies to pH measurement. Thereafter, the sensor unit or sensor arrangement can be replaced. The sensor unit and/or the sensor arrangement therefore need not be particularly robustly designed for reuse, but can be implemented in miniaturized form.

In the event that reagents or the sensor unit as a whole are consumed and/or destroyed during measurement, interchangeability is particularly advantageous.

Advantageously, the brush head can have a so-called sensor adapter, in particular a one-, two-, or three-way adapter (three-way connector) for linking the interchangeable sensor unit or the interchangeable sensor arrangement, e.g., a biosensor, to the brush head.

The brush head can preferably have an electrical interface with contacts, in particular in the form of spherical, preferably gold-plated, contact elements, which are arranged as a matrix. The matrix can have a linear 1-dimensional array or be designed as a 2-dimensional matrix. Preferably, the matrix is sealed against liquids, including saliva or saliva with a corresponding IP class, e.g., IP67. Preferably, so-called BGA contacts (ball grid array or ball grid structure) are provided as contact elements. In addition, or as an alternative to the aforementioned BGA contacts, pins and/or lamellae can also be provided. Thus, a total of several connector/interface contacts, preferably in the form of BGA contacts, pins and/or lamellae, can be provided.

The brush head, in particular the sensor unit or sensor arrangement, can have at least one reservoir and/or supply line for delivery substances, in particular of biomarkers, e.g., functional molecules, binding substances, e.g., binding ligands, and/or indicator compounds, e.g., luminophores, in particular fluorophores. In the case of binding ligands, these can form a bond with other molecules in the saliva and with the sensor surface. Corresponding ligand-receptor interactions and the corresponding binding molecules are known from the field of application of ELISA tests (enzyme-linked immunosorbent assays) and can also be used as binding ligands in the context of the present invention.

It is advantageous if the sensor unit, or particularly preferably the sensor arrangement comprising several sensor units, is designed as a thin-layer or thin-film sensor unit or arrangement or as a sensor chip. In this way, miniaturization of the sensor arrangement is achieved and the brush head only has to provide a small amount of space for the sensor arrangement or sensor unit. Alternatively, or additionally, the sensor arrangement can be formed additively and/or subtractively by means of a microtechnology process, e.g., manufactured by means of lithography, soft lithography, 3D printing, printing, screen printing, and/or stereolithography.

The sensor arrangement can advantageously have at least two, preferably at least three, sensor units for determining at least two substance properties of saliva, preferably three substance properties of saliva, in particular at least one physical substance property and at least one chemical, biochemical and/or biological substance property. A tendency to disease formation can be derived from the determined substance properties.

The sensor arrangement can have a first sensor unit for determining a voltage-equivalent measured value of the medium or the saliva, in particular a resistance value of the medium or a conductivity value of the medium. The first sensor unit may additionally or alternatively be designed to perform an impedance measurement of the saliva with one or more frequencies and/or frequency bands, and/or a current- or charge-based dynamic measurement. A potentiostatic measurement is also possible.

In particular, the first sensor unit can determine an electrical impedance value, wherein the impedance values can preferably be determined over several frequencies and/or frequency bands. The DC resistance is included in the impedance as a DC value. The effective resistance R is the frequency-independent, real part of the complex impedance $Z(f)=R+jX(f)$. Coated electrodes and electrolytes lead to complex impedances of biosensors because of their capacitive properties (charging of electrodes, electrode surfaces, insulations, permittivity of electrolyte/body fluids). Also, a temporal (dynamic) voltage and/or current measurement and/or a charge measurement (Coulomb) could be taken to determine the voltage-equivalent resistance value. A model-based determination of the aforementioned quantities can also be carried out.

The sensor arrangement advantageously has at least a second sensor unit for determining the pH value of saliva.

Also advantageously, the sensor arrangement can have a third sensor unit, wherein the third sensor unit is designed as a biosensor. An electrical brush head is usually used over longer periods of time e.g., 30-80 days, which is not a realistic application period in the case of biosensors with coated electrodes or even optical sensors. The measurements lose accuracy, stability, specificity, selectivity and can become unusable after only a few days.

In a preferred embodiment variant of the invention, the biosensor is formed as a hormone, enzyme, peptide, and/or protein sensor, including an antigen and/or antibody sensor, and more preferably as a lactate sensor, a glucose sensor, a GABA sensor, an IgA sensor, a lysozyme sensor, an IgG sensor, an IgM sensor, IL-6 sensor, CRP sensor, Tnf-a sensor, and/or an alpha macroglobulin sensor. These compounds are indicators of periodontitis, parodontitis, diabetes, and/or cardiovascular disease. Alternatively, or additionally, the biosensor may be formed as one or more sensors for the detection of metabolites of disease.

Disease-causing bacteria can be understood as preferably periodontitis- and/or caries-causing bacteria, preferably *Prevotella intermedia, Porphyromonas gingivalis, Tannerella forsythia, Treponema denticola,* and *Aggregatibacter actinomycetemcomitans* associated with aggressive periodontitis, which produce metabolites that are detectable. However, metabolites of other diseases, for example, viruses such as SARS covid or influenza viruses, as well as other pathogens of colds or oral tracheal carcinomas can also be measured. Also, various pathogens such as bacteria, viruses as well as fungi, especially mold, are detectable.

Preferably, the third sensor unit or additional sensor units can detect different metabolites or analytes per clinical picture in order to exclude a false-negative measurement.

The sensor arrangement and/or an individual sensor unit can be positively or non-positively arranged on the side of the brush head facing away from the bristle, for example by clamping, latching and/or pressing.

Furthermore, a mechanical and/or electrical interface, e.g., including the aforementioned adapter, may be provided. At the location, a locking mechanism may be provided between the sensor arrangement and/or the sensor unit and the brush head so that replacement is only possible after actuation of the locking mechanism.

During signal processing, raw signals or raw data can preferably also be processed with a sufficiently high sampling—preferably in the range 10 to 1000 Hz and over longer time periods, preferably of at least one minute. The time period can also be more than 4 minutes and the sampling can be done depending on the state of toothbrush. For example, if scanning is performed during ultrasonic wave treatment by an electric toothbrush, a different time period can be selected in the resting state than in the mode in which vibrations are active (to avoid the interfering influence of vibrations on SU measurement). In the case of sampling during active vibrations, advanced signal processing (DSP) can also be used to filter out or compensate for the disturbances, so that disturbance or sport magnitude switching or compensation is performed. For this purpose, perturbations can be estimated or determined and the signals compensated and/or adapted as in a feedforward-disturbance compensation scheme (known from control engineering) or adaptive noise canceller (known from DSP—Digital Signal Processing: Adaptive Noise Canceller by Widrow, Echo-Cancellers, adaptive LMS filters) scheme.

The interchangeable sensor unit with biosensors will provide electrochemical signals according to the developed redox reactions, developed in a preferably specific manner to the target biomarker biosensors. Since this unit should provide readings, preferably over multiple measurements and/or multiple days, in a reliable manner (with suitable precision and stability), advanced signal processing methods are advantageous.

A variety of current electrochemical biosensors typically require preconditioning in a suitable solution prior to measurement, over time intervals of 10-30 minutes.

Alternatively, or additionally, the sensor arrangement may also comprise electro-optical sensors by means of which a change in fluorescence or a spectral change or a change in the refractive index (RI index/refractive index) can be detected.

In the present application, preconditioning can be shortened in the application cycles or it can advantageously be omitted. Preconditioning may be easier to implement in the device with an exchange station, but more difficult without such an exchange station, i.e., in an electronic toothbrush without a corresponding exchange or charging station, i.e., as a stand-alone SU unit. However, one can also advantageously bypass preconditioning by using one or a combination of several DSP methods. These can also be used for further functionality of the product, such as detection of the state of biosensors—dry vs. wetted with saliva, detection of good signal quality vs. poor signal quality e.g., also detection of intermediate states where the SU unit is not sufficiently wetted with saliva, or movements are detected that cause disturbances.

Furthermore, exemplary embodiments of the invention are directed to a toothbrush with a brush head according to the invention.

The toothbrush can advantageously have a control and/or evaluation unit which is equipped to acquire data, in particular raw data, during the measurement of the saliva by the sensor unit at a sampling rate of 10-1000 Hz.

The control and/or evaluation unit may further be equipped to acquire data, in particular raw data, during the measurement of the saliva by the sensor unit in a sampling interval of at least 3 to 500 seconds.

Furthermore, the toothbrush can have a radio module for data transmission with an external device for data processing under determination of a health condition. The radio module may be part of an electronics module, which may further include a measurement module. The electronics module may include one or more ASICs as application-specific integrated circuits.

Alternatively, or additionally, the toothbrush can have a module for inductive power transmission, which is preferably arranged in the handle of the toothbrush.

Furthermore, according to the invention, an analysis system can be considered comprising the toothbrush according to the invention and an external device for data processing, wherein raw signals are transmitted from the toothbrush to the external device and wherein the external device has a data memory on which a computer program product for data analysis is stored, wherein the computer program product is designed for data analysis of the data determined by the sensor unit, preferably according to one or more DSP methods (digital signal processing method), for determining a state of health.

A method for the operation of an analysis system according to the invention comprises data analysis and has the following steps:
  a) Sampling of electrochemical signals, in particular of amperometric signals at different potentials and/or voltametric signals at different currents, and/or impedance signals over a measuring period with a predetermined sampling rate The preferred measurement duration and sampling rate have been described previously.
  b) Detection and classification of states of the sensor element with respect to the "wetting state" based on the detected electrochemical signals and/or impedances.

In a preferred embodiment variant, the aforementioned detection can be performed by an impedance measurement. The following values were detected in a frequency range between 500 Hz to 100 kHz. The values can vary with the frequency.
Saliva: typical range: 0.6-1 kOhm
Saliva with water: 1-1.6 kOhm Exclusively water will show much higher values because it does not conduct as well. Values of 3-8 kOhm are assumed for tap water.

Toothpaste in saliva reduces the impedance values to 0.2-0.5 kOhm; the reductions depend on the composition of the toothpaste and the amount used, the more toothpaste the greater the reduction in impedance values.

Thus, one can use the impedance measurement described above to detect the following conditions: Water over sensors (full or partial wetting of sensors), water-saliva mix, saliva, saliva with toothpaste
  c) Evaluation of amplitudes and changes of the electrochemical signals and/or impedances and in particular the associated redox reactions and/or capacitive transients in order to analyze the saliva with regard to the health status of the user The evaluation can be carried out in particular by an actual value and setpoint comparison by an evaluation unit, wherein predefined data sets for the evaluation are stored in a data memory of the evaluation unit, e.g., in so-called look-up tables.

It is particularly advantageous if in step c) a decomposition and/or filtering of the sampled electrochemical signals into a useful component and one or more interfering components of the signal takes place, wherein the useful component represents or correlates with the redox reaction component of the signal, which is relevant for the concentration determination of biomarkers. The correlation may be, for example, linear or exponential or the like.

The method, in particular following step c) or preceding step a), may comprise at least one of the further steps:
  d) Sampling of electrochemical signals after conditioning and/or stabilization in a provided reference solution; and/or
  e) Repeating measurements to combine information from multiple measurements, preferably to improve precision, improve the signal-to-noise (S/N) ratio, and/or compensate for interference.

Also, according to the invention, an exchange station for the exchange of the brush head can be regarded as having an exchange chamber, wherein the brush head can be inserted at least regionally into the exchange chamber, and wherein the exchange station has a supply arrangement with a plurality of separable sensor arrangements and/or sensor units and a fitting unit for fitting the brush head within the exchange chamber. The exchange chamber is open to at least one side for insertion of the brush head.

Loading can, for example, take place automatically or by manual application of force. Many variants can be considered for the exchange station. For example, the exchange station can be either a table-top size or a small hand-operated station. In particular, in the latter case, the station may be powered by a battery or other portable power storage device, such as a rechargeable battery.

Further advantageously, the exchange station may comprise a radio module, e.g., a wireless transmitting and receiving unit, for bidirectional wireless data exchange, in particular with an external computer or server or a cloud application.

An exchange station can optionally have sensors that evaluate saliva samples collected by the brush head itself. For this purpose, the exchange station can have one or more fluid lines for flushing a measuring chamber into which the saliva sample is introduced, and one or more fluid lines for adding reagents to the measuring chamber, as well as a measuring and evaluation unit which evaluates the measured values recorded by the sensors of the exchange station. The measuring chamber can also be the exchange chamber. By means of a mechanism, preferably a mechanism as described above, the toothbrush, in particular its bristles, or its pad, sponge, or other material can also deliver an active substance.

Another concept of the present invention is that the station does not exchange sensor units or sensor arrangements, but rather operates as a storage station merely evaluating saliva collected by the toothbrush. This collection of saliva is carried out via a suction mechanism within the toothbrush. This saliva is then delivered to the measuring chamber and evaluated within the measuring chamber by at least partially exchangeable sensors arranged for this purpose.

The exchange station can advantageously have a charging station, e.g., a charging connection point, for charging the toothbrush.

Furthermore, the exchange station can have a collection and/or evaluation unit for reading out sensor data of the used sensor arrangement and/or for calibration or for reading in sensor data for the sensor arrangement to be equipped.

It is advantageous if the exchange station and/or the toothbrush has at least one transmitter module, in particular a transmitting and receiving module, for data exchange of determined sensor data with an external data processing unit. Here, for example, a Bluetooth module, an NFC module, an RFID module, a LoRa module, a 5G module, or the like can be considered.

In the case of the transmitting and receiving module or an additional receiving module, bidirectional data exchange can take place.

The exchange station can have a module for wireless power transfer, e.g., by inductive power transfer. This module can also perform a data transfer, so that the module can advantageously also assume the function of a transmitting and/or receiving module. A module for wireless energy transfer can also be additionally contained in the toothbrush handle and/or in the toothbrush attachment.

Various data can thus be read from the toothbrush, the sensor arrangement, or the respective interchangeable sensor unit. This includes, for example, calibration data, UDI data (i.e., a serial number or other data for identifying the toothbrush and/or the sensor arrangement and/or the sensor unit), configuration data and, obviously, sensor data, e.g., measured values or measurement conditions. Further preferably, QAM, FSK or PSK can be used for data transmission.

The data exchange is preferably bidirectional between the exchange station and the brush head. For this purpose, the brush head or toothbrush can have a microcontroller preferably with EEprom (electrically erasable, programmable read-only memory). In addition, the brush head or toothbrush may have another non-volatile RAM memory. This memory may be located in an optional ASIC chip, separately in the microcontroller, or in other electronic components of the brush head or toothbrush.

The exchange station can have further optional units that expand the analysis variants and/or the operability of the toothbrush. Furthermore, measurement conditions as well as states of the electronics or device states can be set and checked. For example, the exchange station can have a recognition unit that recognizes the identity of the toothbrush or the user associated with it and makes the setting individually to this person. For this purpose, the toothbrush has a marking, e.g., a QR code or the like.

An evaluation unit provided in the exchange station according to the invention or in the toothbrush according to the invention may be designed for carrying out a method according to the invention for operating a toothbrush according to the invention for monitoring the state of health, in particular with regard to the formation of periodontitis, in a user or patient, the method comprising the following steps:

I. Equipping the brush head of the toothbrush with a new sensor arrangement and/or sensor unit, in particular in the exchange station;

II. Inserting the brush head into the oral cavity and contacting the sensor arrangement and/or sensor unit with saliva;

This consumes the sensor arrangement and/or sensor unit. Consumption can occur in particular after a single contact.

III. Generating sensor data for determining at least two, preferably at least three, substance properties of the saliva, and IV. Removing a used sensor arrangement and/or sensor unit and reading out the data, in particular within the exchange station.

Some of the steps, e.g., step III and IV, can be performed simultaneously. In step I, moreover, a calibration of the sensor units can optionally and advantageously take place. The process itself is also considered to be according to the invention.

Of course, only one or more substance properties can be determined as a sum, wherein the substance properties can be sum parameters, which can be determined based on a model. It is also possible to determine only the change in the substance properties. This also falls under the aforementioned step III. Furthermore, additional biomarkers from external devices can be processed and, in particular, included in the sum parameter. A typical example of this is the data from the Applehealth Vital Signs program.

After performing step II of the method, an indicator module may indicate that the sensor arrangement is depleted and needs to be replaced to repeat the method. However, the use of the indication module is not mandatory when carrying out the method according to the invention. The indication may be, for example, acoustic, optical (e.g., by an LED display or a display e.g., a display on the device itself or on a mobile device such as a smartphone) or by vibration.

Furthermore, a device for monitoring the state of health, in particular with regard to the formation of periodontitis, parodontitis, diabetes, or cardiovascular diseases in a user, can be regarded as a subject matter according to the invention, comprising a toothbrush having a device for extracting saliva from a patient and a station with a measuring chamber for receiving the extracted saliva, wherein at least one sensor unit or a sensor arrangement comprising at least one sensor unit is arranged within the measuring chamber and wherein the sensor unit or the sensor arrangement is arranged interchangeably within the measuring chamber. In this case, the station is not an exchange station for replacing the sensor assembly or sensor unit on the brush head, but the sensor unit or sensor assembly is arranged within the measurement chamber or replacement chamber. For contact with the patient's saliva, the toothbrush is used in this case only as a means of transport. The generation of measurement data therefore does not take place in the patient's mouth, but only within the station.

It is particularly advantageous in this concept if the measuring chamber has a supply, in particular a magazine, of unused sensor units or sensor arrangements and has an exchange mechanism, e.g., a removal and fitting machine, for exchanging a used sensor unit or sensor arrangement for a new sensor unit or sensor arrangement from the supply or magazine.

The device for extracting the saliva in the toothbrush may preferably be designed as an aspiration device and may comprise, for example, an aspiration pump and/or dispensing pump, e.g., for transporting and administering liquids.

In an advantageous variant of the method, after step II of the method has been carried out, the sensor arrangement is used up and must preferably be replaced to repeat the method. This variant is usually described as "single-use" or one-time use.

Further according to the invention is the use of the brush head according to the invention for monitoring the health status, in particular the concentration of viruses, bacteria in the body, the inflammatory status in the body, the risk of diabetes and/or carcinoma, the risk of cardiovascular disease and/or the fertility cycle, of a user.

BRIEF DESCRIPTION OF THE DRAWING FIGURES

In the following, the invention is explained in more detail with reference to an exemplary embodiment with the aid of figures. Variations of the exemplary embodiment are also mentioned and can be understood as isolated features.

FIG. 9 shows a schematic representation of a fifth embodiment variant of a brush head according to the invention;

FIG. 10 shows a further view of the brush head of FIG. 9;

DETAILED DESCRIPTION

Figure 1:
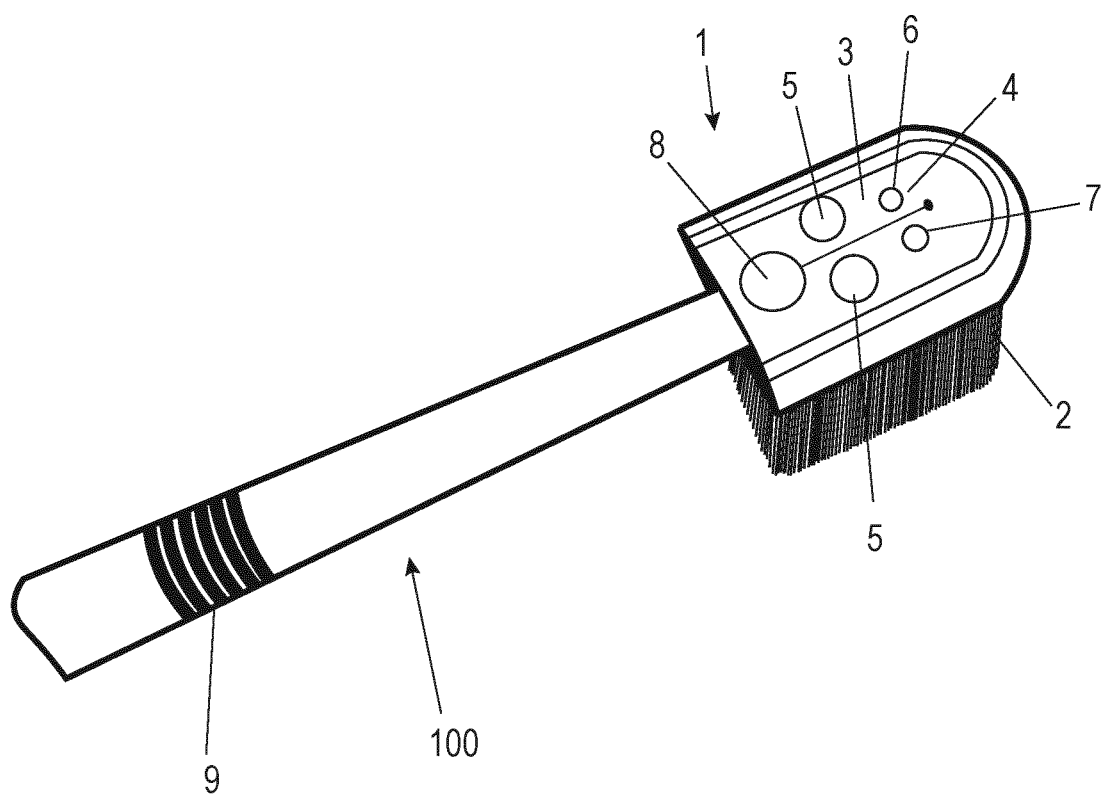
FIG. 1 shows a schematic representation of a brush head of a toothbrush according to the invention.

FIG. 1 shows a brush head 1 of a toothbrush 100 according to the invention. In the present case, the brush head 1 is that of an electric toothbrush. Obviously, it can also be a toothbrush without an electric drive for moving the brushes and/or without an ultrasonic transmitter. In this case, a power supply unit is required, but this only operates the sensor units, in particular the biosensor and electrosensor systems, optionally transmitting and/or receiving modules and optionally an evaluation unit.

The brush head 1 has a plurality of bristles 2 at the front and an exchangeable sensor arrangement 3 comprising several sensor units at the rear. The sensor arrangement 3 is designed as a flexible plastic film or as a chip on a plastic substrate and comprises at least one first sensor unit 4 for determining the pH value of the measured medium. This is preferably a disposable sensor unit, in particular for single-use. The sensor unit may in particular be designed as a thin-foil and/or thin-film sensor unit or as another form of sensor unit based on microtechnology, for example as a MEMS unit. Further variants for forming a corresponding sensor unit are, for example, 3D printing, pad printing, lithography, or screen printing.

Furthermore, the brush head 1 can have a sensor adapter, in particular a one-, two-, or three-way adapter for linking the interchangeable sensor arrangement 3, which, however, is arranged below the sensor arrangement and thus concealed in FIG. 1.

Typical thin-film sensor units for measuring pH are, for example, carbon electrodes doped with ruthenium dioxide. Such pH electrodes are described as disposable sensors for single use e.g., by Koncki et al, in "Disposable screen-printed pH-electrode for determination of anticholinesterase activity" (p. 139 ff. Biosensors for Direct Monitoring of Environmental Pollutants in Field).

Other pH thin-film sensors with pH electrodes based on ISFET technology are also known per se from various applications. An exemplary design of a pH sensor with a reference electrode and an additional electrode is described, for example, in DE 10 2011 085 747 A1.

AT186493 A, AT 184692 A and DE 10 2006 022 290 also disclose pH sensors based on thin-film technology or thick-film technology with electrode layers, in particular conductive and semiconductive layers of different materials or sensor chips.

The design of the first sensor unit is not necessarily limited to the two electrodes shown. For example, the sensor unit can preferably be designed as a potentiostat arrangement with a working electrode, a reference electrode, and a counter electrode.

The use of a so-called 3-electrode cell is also possible within the scope of the present invention, whereby in a particularly preferred embodiment a fourth and possibly further electrodes can be used in the sensor units for disturbance detection and disturbance compensation. In a signal processing procedure carried out by an evaluation unit, such as disturbance compensations for noise reduction, take place.

Preferably, the aforementioned sensor unit(s) and the aforementioned pH sensors and associated electrical leads and connections may be disposed on or in a flexprint circuit board or flexible film.

As a measuring range of the pH sensor, a pH value between 1-13, preferably between 3-8, is recommended for the application. Saliva is known to be neutral to weakly basic, so that the aforementioned measuring range is ideal for the application. It is also advantageous if the sensor unit 4 itself has a temperature sensor, not shown more closely, for determining the temperature of the medium. Insofar as this lies outside a predetermined measuring range, in particular between 33 to 37.5° C., for example due to ice, tea or the like, there can optionally be an error output for the measurement with the indication that the temperature in the throat is outside a predetermined specification range, or there can be an indication of a physiological change, e.g., pregnancy, illness, or reaction, e.g., immune reaction, due to increased temperature or fever from 38.5° C. Temperature measurement over days can also be beneficial for health status monitoring including a personalized profile and/or fertility cycle determination, e.g., for contraception or fertility determination.

The maximum extension of the aforementioned sensor unit in a spatial direction can preferably be between 4-8 mm.

Preferably, the sensor unit may have a spatial dimension of less than 150 mm$^2$, more preferably between 50-120 mm$^2$.

The thickness of the sensor unit can be less than 4 mm, preferably 2 mm or less. Particularly preferably, the respective sensors can be arranged, in particular printed, on a film as substrate.

The sensor unit, as a film can preferably be changed after a maximum of 15 times use, preferably a maximum of 10 times use.

The individual sensors of a sensor unit can be round, wherein at least one or some of the sensors can be designed with a diameter between 1-3 mm.

A control and/or evaluation unit integrated in the toothbrush (in the brush head or in the brush handle) (not shown here) can be equipped to acquire data, in particular raw data, during the measurement of the saliva by the sensor unit 4, 5, 8 in a sampling interval of at least 3 to 500 seconds. However, a measurement period of less than 20 seconds is advantageous, for example 5 seconds.

Furthermore, the sensor arrangement 3 comprises a second sensor unit 5, preferably a thin-film sensor unit, for determining a voltage or a voltage-equivalent measurand. In this case, the second thin-film sensor unit comprises a pair of electrodes consisting of two electrodes 6 and 7 for determining the measurand, such as the conductivity of the measuring medium, the impedance of the measuring medium, the current intensity or also the voltage, or a respective drop between the electrodes. Especially preferred is the impedance measurement at one or more frequencies, for example frequency ranges, 0.1 to 100, from 100 to 5000 Hz, and from 1 kHz to 10 kHz, optionally even higher.

Instead of the two electrodes 6 and 7, a potentiostat or a 3-electrode arrangement can also be provided as sensor unit 5. An impedance measurement can be used, for example, to measure biomarkers such as TNF-a or other biomarkers.

This second sensor unit 5 is also spaced at a small distance of less than 1 cm, preferably less than 5 mm, particularly preferably less than 3 mm, from the first sensor unit 4. Since the composition of the medium in the oral cavity can change, this small distance is preferred so that the sensor units essentially analyze saliva of the same composition.

The sensor arrangement 3 also has a third sensor unit 8. The third sensor unit 8 comprises a measuring cell and a reference cell for determining a substance concentration of a chemical compound in saliva. The chemical compound that can be determined is, for example, the lactate or glucose content. The measuring range of a glucose sensor is between 0.1 and 1 mM. The measuring range of a lactate sensor is between 0.025 to 0.5 mM.

Other variations of sensors for the third sensor unit 8 include enzyme sensors, peptide sensors, protein sensors, or cell detection sensors.

The third sensor unit may be designed as a so-called GABA sensor (gamma-aminobutyrate acid), an IgA (immunoglobulin A), IgG, IgM, CRP, and/or a lysozyme sensor. This third sensor unit, by determining the concentration of at least one chemical compound, makes it possible to detect the presence of other diseases that would interfere with the measurement of the first and second sensor units. A typical sensor for determining the aforementioned quantities is, for example, an electrochemical sensor, an optical sensor, or one or more suitable coated biosensors.

The brush head according to the invention additionally permits determination of the presence and concentration of anaerobic and/or aerobic bacteria or individual classes of the aforementioned bacteria, e.g., by measuring the concentration of their degradation products and/or metabolites, and permits evaluation of the state of the immune system. By suitable combination of the above-mentioned sensors and detection or non-detection of bacterial metabolites, an infection by viruses can be concluded. This is particularly the case if infection values or infection criteria are fulfilled and detected, but the bacterial metabolites are not detected.

In the preferred embodiment variant of FIG. 1, the brush head 1 has a mechanical interface 9 for releasable connection to a handle 101, in particular a drive device of an electric toothbrush 1.

Figure 2:
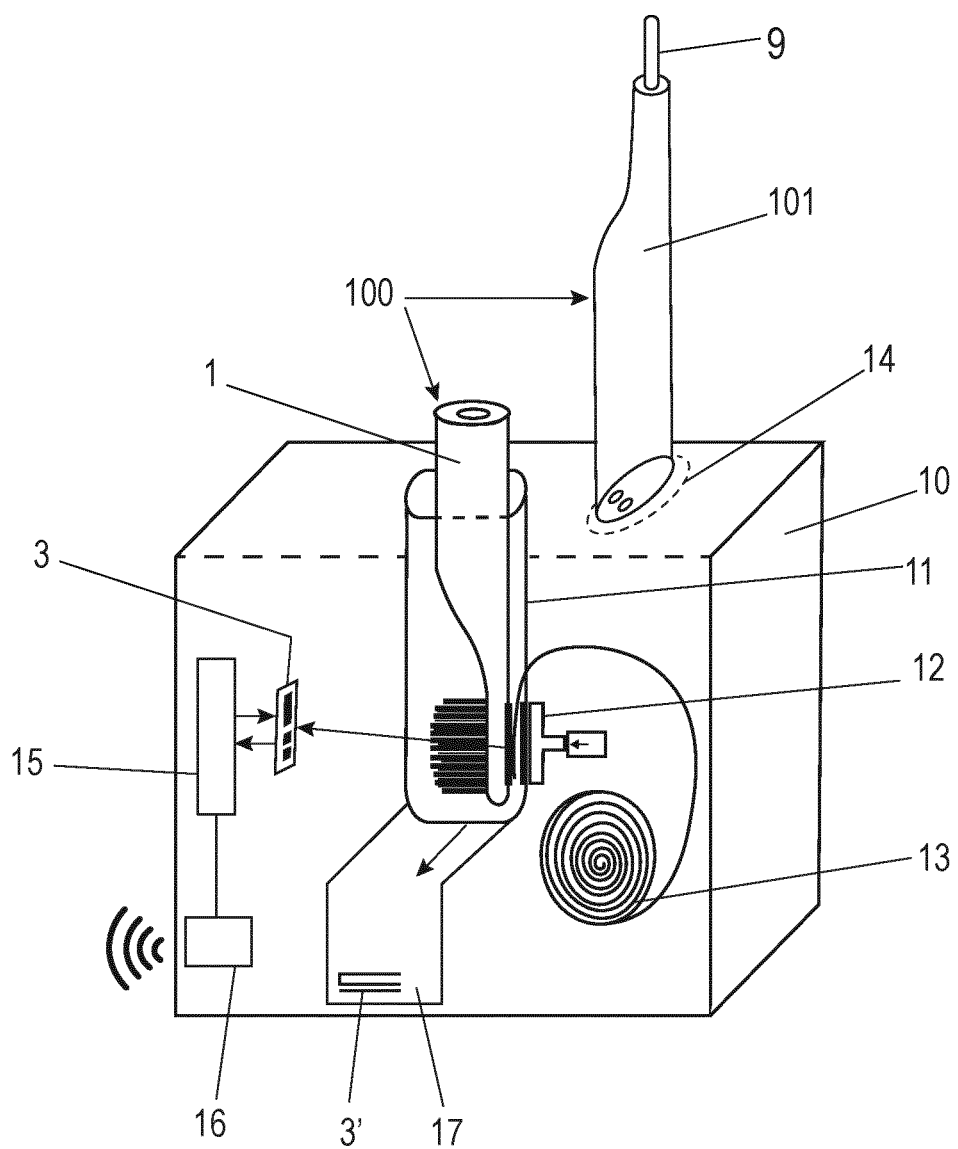
FIG. 2 shows a schematic representation of an arrangement according to the invention comprising an exchange station and the brush head of FIG. 1.

FIG. 2 shows a preferred variant of an exchange station 10 for replacing the sensor arrangement 3 on the back of the brush head 1. However, other variants of exchange stations 10 are also possible within the scope of the present invention.

The exchange station 10 comprises an exchange chamber 11 into which the brush head 1 can be inserted. In this exchange chamber, a separation of the used sensor arrangement 3 and the provision with a new sensor arrangement 3' takes place. This new sensor arrangement can be separated as a discrete section of a supply arrangement 13, e.g., a film roll or a magazine, by a separating device 12. Subsequently, a loading of the brush head 1 can take place. In the case of FIG. 1, the separating device 12 is advantageously in compact design at the same time the loading device. However, it is also possible that both aforementioned devices are arranged separately. In a first step, the placement device can remove the used sensor arrangement 3', e.g., by suction or magnetic detachment or the like, and in a second step equip the new sensor arrangement 3.

A reservoir 17 is provided below the replacement chamber for storing the spent sensor arrangements 3.

As an alternative to the film roll, a magazine with several chips can also be arranged in the exchange station 10, wherein the chips do not necessarily have to be of flexible design.

The exchange station 10 can also have an integrated charging station 14 in which the handle of the electric toothbrush can be charged, in particular inductively.

In an optional readout and/or evaluation unit 15, the sensor data of the consumed sensor arrangement 3 can be read out and evaluated if necessary. The sensor arrangement can be read out to store the sensor data. Subsequently, the read-out sensor data can be transferred to an external data processing unit, e.g., a database of a dentist or to a computer.

For this purpose, the exchange station 10 has at least one transmitting module 16, in particular as a transmitting and receiving module, for wireless connection to the data processing unit. If the transmitting module 16 is designed as a transmitting and receiving module or a receiving module is provided in addition to the transmitting module 16, a software update of the evaluation unit 15 can also be performed. Suitable technologies for data transmission are, for example, 5G, LoRA, BT, NFC, via a hub or mobile device or directly via a base station (LoRA, or 5G or 4G/cat-M, LTE Cat M1).

It is of course also possible that the data determined by the sensor arrangement 3 is not only transmitted in the exchange station 10, but that a data transmission is already carried out by the toothbrush 100.

The exchange chamber 11 can be flooded with a cleaning medium and/or water for cleaning, so that the brush head can be cleaned. If the exchange chamber 11 is also used as a measuring chamber, rinsing can be carried out to produce measuring conditions that are as constant as possible. In addition, reagents can be added to the measuring chamber.

Provided that the toothbrush 100 has a supply of a toothbrushing or mouth rinsing medium, the exchange station 10 can have a reservoir for the toothbrushing or mouth rinsing medium and supply it to the toothbrush 100, for example via the charging station 14, for filling the toothbrush 100.

Alternatively, the application of toothpaste to the bristles of the toothbrush can also be carried out directly by the exchange station.

Furthermore, the exchange chamber 11 or a chamber which is fluid-mechanically connected to the exchange chamber 11 can have a sensor arrangement, e.g., for an optical measurement. A suction device can optionally be provided for transfer to the additional chamber.

The saliva adhering to the brush head 2 can be diluted and/or limited to a predefined volume, e.g., the chamber volume, and subsequently measured optically, electrochemically, or physically. For this purpose, a supply line for delivery substances, e.g., functional molecules, binding substances, e.g., binding ligands, and/or indicator compounds, e.g., luminophores, in particular fluorophores, may be provided, a light source for emitting a light for exciting the indicator compound with at least one wavelength, and a receiving unit for measuring the received light. Accordingly, a fluorescence spectroscopic examination, a UV-Vis spectroscopic examination and other optical analysis methods can be applied by optical sensor technology.

It can occur that the toothbrushing or cleaning medium interferes with individual measurements. It is therefore advisable to perform a reference measurement without saliva from time to time. This enables the evaluation unit to quantify the amount of toothbrush or cleaning medium used in the saliva when measuring a saliva sample after brushing the teeth and to compensate for the resulting interference in the measurement signal. This can alternatively or additionally be carried out in a model-based manner on the basis of stored parameters or by non-parametric model-based methods or by population counting, e.g., of bacteria.

Alternatively, this reference measurement can also be omitted, e.g., if the respective analysis method is insensitive to interference or if the same tooth cleaning or cleaning medium is always used for which the manufacturer has already stored a data record in the data memory of the evaluation unit for measured value compensation.

The determination of the general state of health and specifically the oral state of health within the oral cavity can be carried out on an individual user basis or by estimation on the basis of an average value. In the former case, the state of health must be determined by a physician and, following the examination, a reference measurement must be created and stored for comparison with the data determined by the toothbrush.

In addition to the preferred field of application of early detection of periodontitis (e.g., by measuring IgA), other dental diseases (e.g., by measuring GABA) or even caries (e.g., by measuring Lactobacillus), the present invention can also be used for early detection of individual cancers and/or pregnancy, e.g., by determining the folic acid content.

Other use cases of early detection, which can also be detected within the scope of the present invention, include carcinomas, cardiovascular applications, myocardial infarction, viral diseases, autoimmune diseases, infectious diseases, gastroesophageal reflux disease, arteriosclerosis, sciatica, respiratory problems, in particular caused by respiratory diseases, chronic obstructive pulmonary disease, Alzheimer's disease, multiple sclerosis, general oral health conditions, diabetes, oxygen uptake, cancer, arthritis, and/or malnutrition, especially obesity.

In addition to early detection, the subject matter of the present application can also be used to monitor nutrition during pregnancy. Pregnant women are regularly checked for values such as iron, folic acid, and the like due to the additional demand for nutrients by the unborn child. Here, the composition of saliva can provide information as to whether the daily requirement of individual nutrients has already been reached and is being maintained.

It is also possible to monitor a patient's medication in this way. For this purpose, a saliva sample from the patient prior to medication can serve as a reference, for example.

An advantageous application of the brush head according to the invention comprises monitoring of medication intake by the user (patient adherence/patient compliance monitoring), e.g., in diabetes.

Here, for example, glucose levels should be within a target band, which in more severe cases can only be achieved by regular use of insulin or GLP-1 inhibitors or similar oral medications that lower blood glucose levels in the blood (GLP inhibitors such as Semaglutide from Novo Nordisk).

With the temporal analysis of time series of biosensor data values, it is also possible to detect not only if, but also when, the patient has taken the medication. If the patient does not take the medication, then other values are measured, completely or partially outside of the desired band. The band or target range can be defined, for example, as a band between 70 and 150 mg/dL, which represents the glucose values in the normal case before and after eating.

The station shown in FIG. 2 is designed as an exchange station. In a non-illustrated embodiment variant of the invention, however, it is also possible to arrange the sensor arrangement of the brush head of the toothbrush in the station, in particular in a measuring chamber of the station. In this concept, however, the saliva must be transferred from the oral cavity to the station. For this purpose, the toothbrush can have, for example, a suction device that extracts saliva in the oral cavity in a first operating mode. In an optional second operating mode, the suction device can have a blow-out function to discharge the aspirated saliva into the measuring chamber and measure it there.

Furthermore, the brush head or, in particular, the exchange station can have further sensors which make it possible to detect individual components of a toothpaste, a mouthwash or other compositions for oral care and to carry out a correction of the measured values of the saliva on the basis of this detection.

The exchange station or the other station according to the invention can also have a delivery of a predetermined type and quantity of a composition for oral care, e.g., for application to the toothbrush. This composition may be stored as a data record, e.g., in the data memory of an evaluation unit, with respect to the concentration of its components.

Further embodiment variants of a toothbrush according to the invention are shown in FIGS. 3-11.

Figure 3:
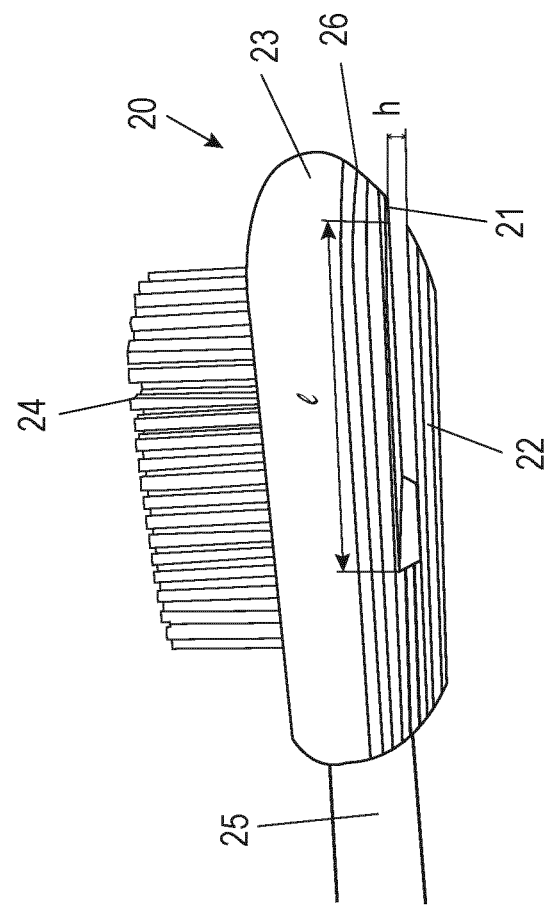
FIG. 3 shows a schematic representation of a second embodiment variant of a brush head according to the invention.
Figure 4:
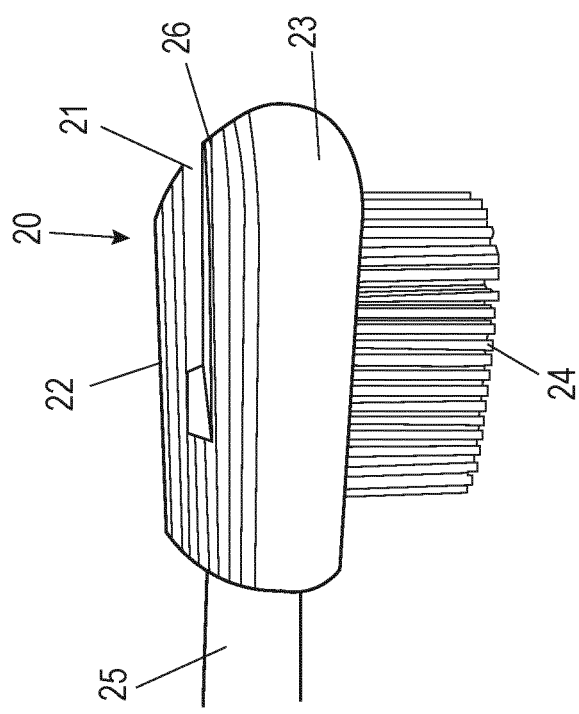
FIG. 4 shows another view of the brush head of FIG. 3.

The variant of a toothbrush head 20 of FIGS. 3 and 4 has a base body 23 from which bristles 24 with an average bristle length l protrude. Bristles 24 of different bristle lengths may be provided, the average bristle length referring to the average value of all bristles.

For reasons of better insertion into the mouth, the base body 23 can have a lower height than the bristle length $l_b$. The bristle length $l_b$ and the height of the base body 23 add up to a total height of the brush head.

Furthermore, the base body 23 has an insertion slot 21 for accommodating a plate-shaped sensor unit. The plate-shaped sensor unit is protected with the two main surfaces from mechanical damage by the base body 23. For this purpose, starting from the position of the bristles 24, the base body 23 has a cover segment 22 at the top. The sensor unit can be inserted into the insertion slot 21 on an end face 26 of the toothbrush 20, wherein the end face is arranged on a side of the toothbrush opposite to a brush neck attachment 25.

The length l of the insertion slot 21 in the insertion direction R is preferably at least 30%, particularly preferably at least 50%, of the length of the brush head in the insertion direction.

The height h of the insertion slot 21 is preferably between 3 and 30% of the height of the base body 23.

Figure 6:
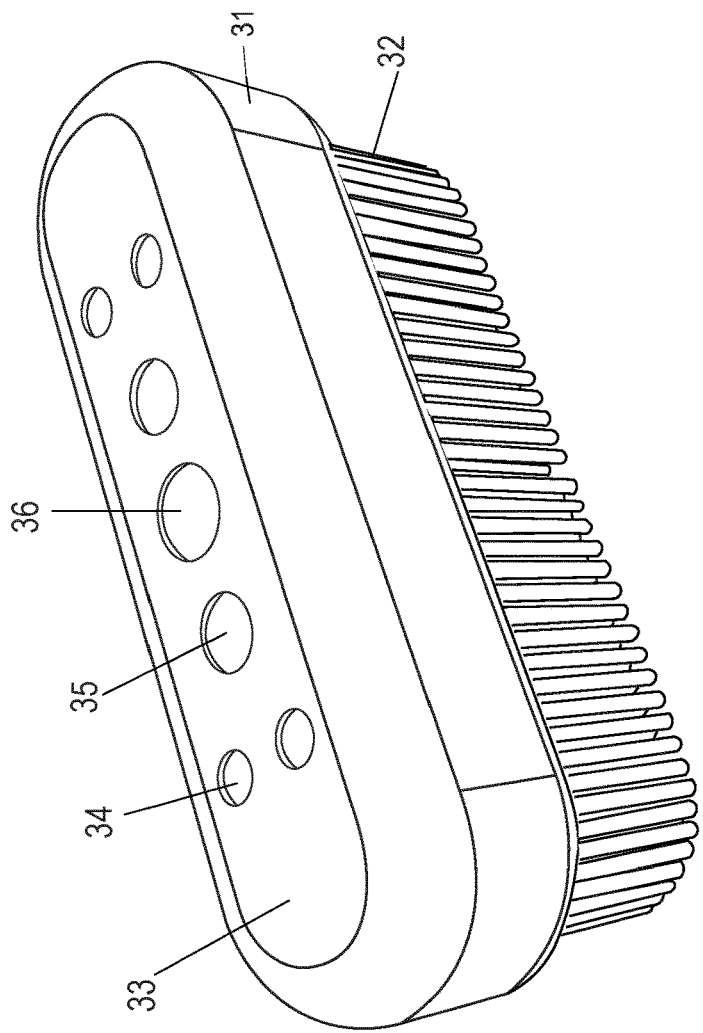
FIG. 6 shows an enlarged view of FIG. 5.
Figure 5:
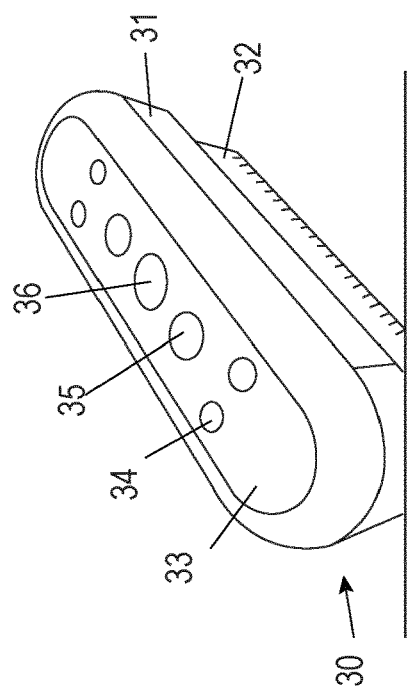
FIG. 5 shows a schematic representation of a third embodiment variant of a brush head according to the invention.
Figure 7:
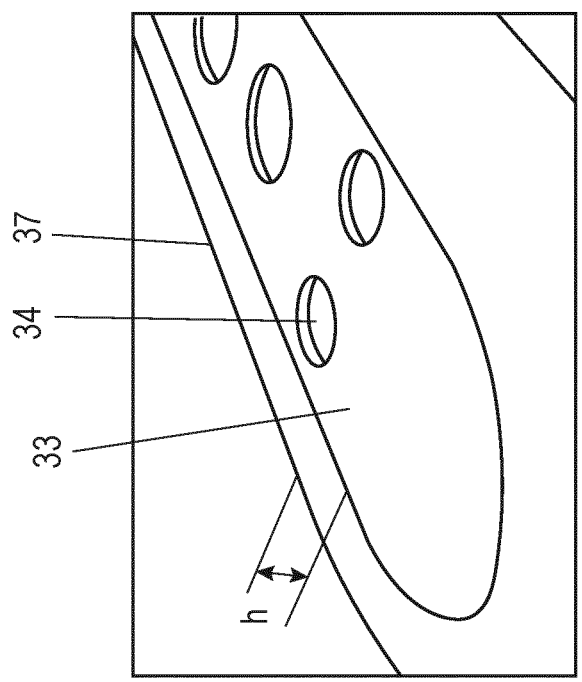
FIG. 7 shows a schematic representation of a section of a fourth embodiment variant according to the invention in variation of the variant of FIGS. 5 and 6
Figure 8:
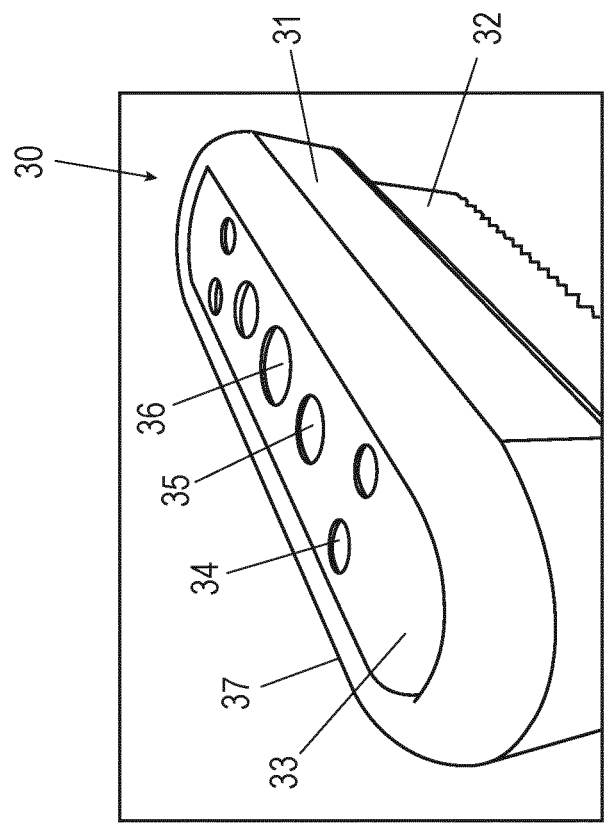
FIG. 8 shows a complete illustration of the variant of FIG. 7.

In a further variant of the present invention shown in FIGS. 5 and 6, a brush head 30 according to the invention also has a base body 31, and bristles 32 projecting therefrom. The rear surface of the brush head opposite the bristles has a support surface 33 and sensor receptacles 34, 35 and 36 recessed therein. These receptacles allow saliva to enter and be positioned during measurement—which is advantageous if saliva contact is too brief. The saliva can enter the receptacles and be held there in contact with the specific sensors, For additional improved retention of the sensor unit, a partial or full perimeter rim 37 may be disposed to the side of and protruding from the support surface 33 so that the sensor unit does not protrude from the toothbrush and allows the sensor unit to be guided and secured during insertion. This tray variant is shown in FIGS. 7 and 8.

Figure 11:
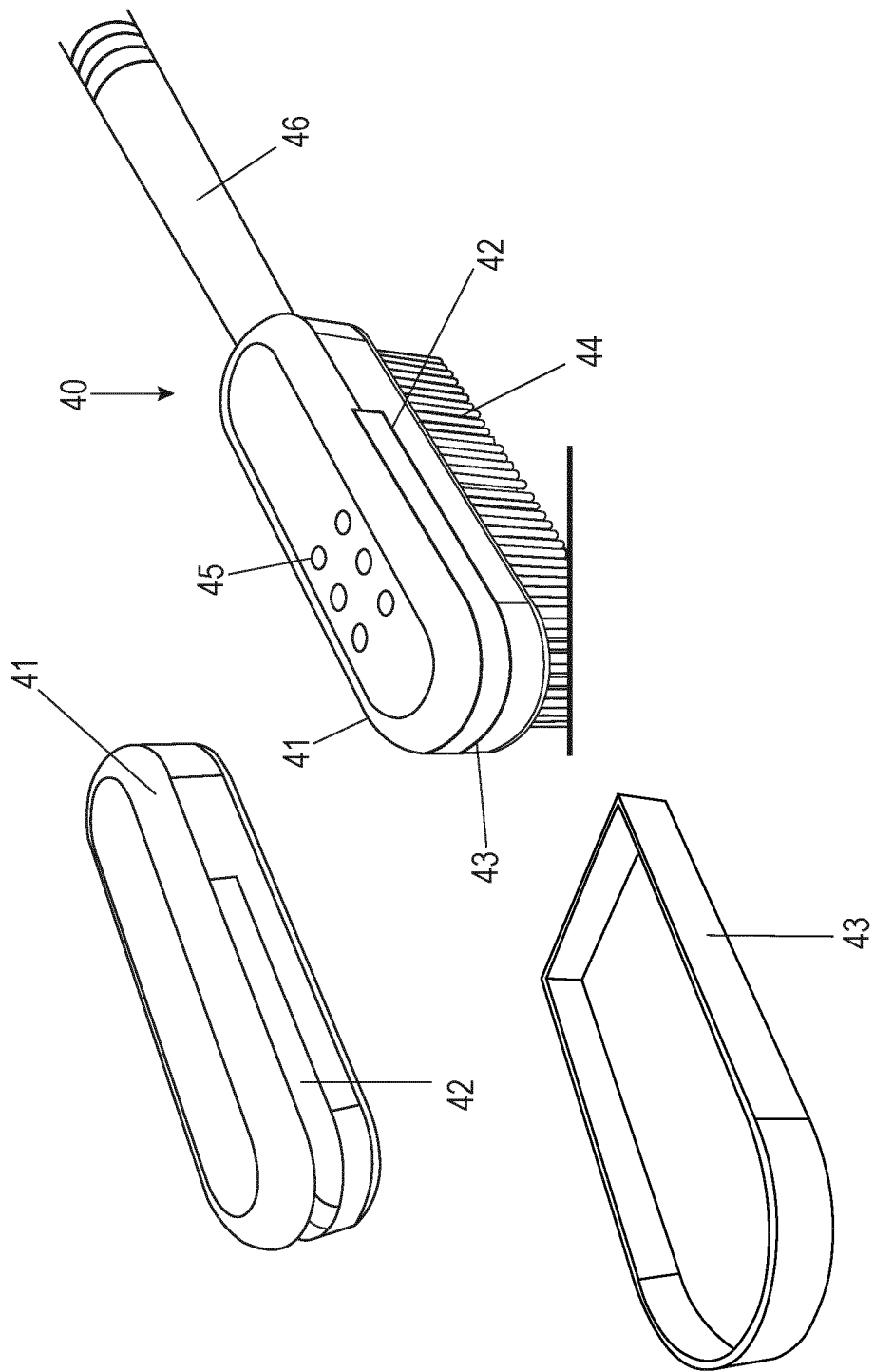
FIG. 11 shows a simplified exploded view of the variant of FIGS. 9 and 10.

FIGS. 9-11 show a further variant of a toothbrush head 40 which, analogous to FIGS. 3 and 4, has a base body 41, an insertion slot 43 for inserting a sensor unit 42, and a cover segment 47. In contrast to the variant of FIGS. 3 and 4, the cover segment 47 has openings 45 for storing saliva. The saliva can pass through the openings 45 and be fed to the respective sensor elements of the sensor unit 43.

The cover may be removable or rotatable away to allow cleaning and drying of the biosensor surface with water and under air.

Other components and features of the toothbrush head shown in the figures are functionally analogous to FIGS. 3 and 4.

Figure 12:
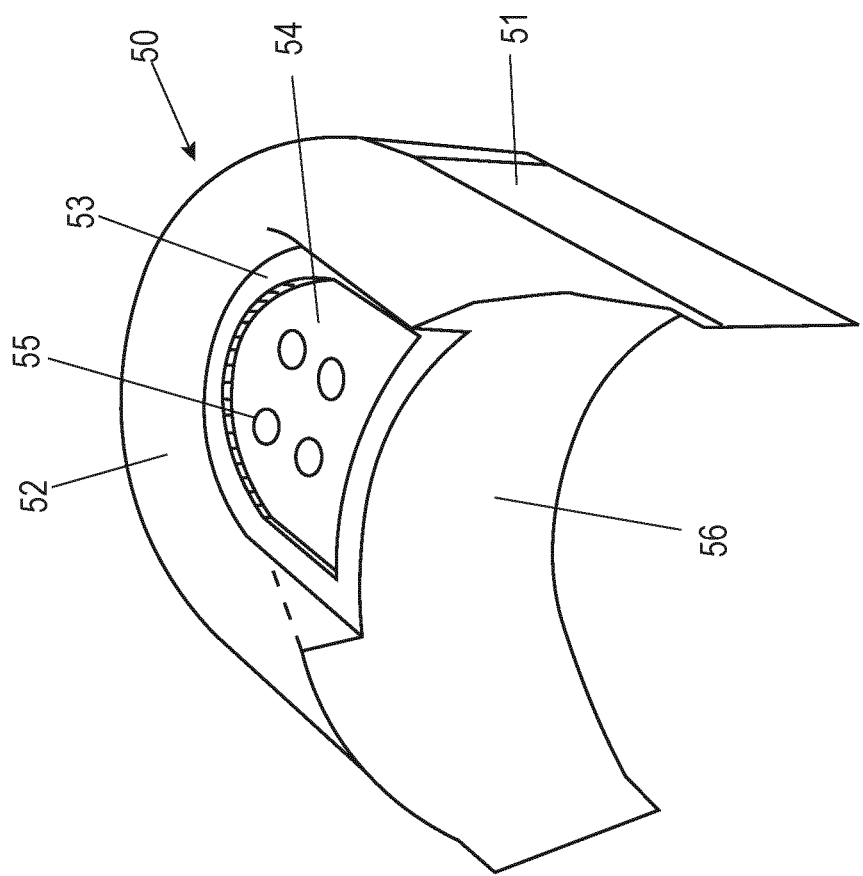
FIG. 12 shows a schematic representation of a sixth embodiment variant of a segment of a brush head according to the invention.

While the sensor unit in FIGS. 3-11 is of flat design, FIG. 12 shows a variant of a brush head 50 having a sensor unit 51 as a lateral attachment to the base body of a brush head. The sensor unit 51 may be part of a larger sensor arrangement, wherein only the sensor unit 51 is interchangeable and the other sensors of the sensor arrangement may be arranged non-interchangeably in the brush head. Such non-interchangeable sensors may be, for example, a temperature sensor or a conductivity sensor, impedance sensors, potentiometric sensors, etc. The exchangeable sensors 55 are recessed in the body of the sensor unit 51, which has a stop surface 56 at the edge of the sensor arrangement 53 for adaptation to the base body. In this variant too, a recess 54 is provided for better accumulation of saliva, as well as a projection 52 on the edge side for the same purpose.

Alternatively, it is also possible to insert a plate-like or film-like exchangeable insert as a sensor unit into the recess 54.

The features of individual embodiment variants can be advantageously combined with one another. The arrangement of the sensor unit on a plane which is recessed relative to the edge region for the accumulation of saliva is particularly preferred (cf. FIG. 8).

The sensor unit is particularly preferably designed as a film and can also preferably be wetted with saliva from one or more sides, preferably completely or at least over the contact area of all sensors.

The sensor unit can be placed or inserted from the side or from above.

The electrical contacts between the brush head and the sensor unit are preferably located in a partial area of a support surface for the sensor unit that is the smallest distance from the brush handle.

Holes are not necessary, but may be provided to collect saliva.

Another aspect is the realization that the influence of toothpaste or toothpaste foam or possibly also mouthwash strongly disturbs the measurement process. Therefore, the measurement should preferably be taken before the actual brushing process. In order to avoid influencing the daily routine too much, the brushing process can already be started and the toothpaste applied after the measurement time, e.g., 5 seconds.

Alternatively, or additionally, a measurement can also be taken after brushing the teeth after rinsing the oral cavity with a calibration rinse.

A method according to the invention for operating an analysis system comprising the toothbrush according to the invention and an external device for data processing. The device may be, for example, a server, a computer, a cell phone, a tablet, and/or the aforementioned exchange station.

Raw signals, e.g., impedance readings, voltage equivalent signals or the like, are transmitted from the toothbrush to the external device.

The external device comprises a data memory on which is stored a computer program product for data analysis, wherein the computer program product is adapted for data analysis of data obtained from the sensor unit, preferably by one or more DSP methods, to determine a state of health.

The data analysis has, according to the method according to the invention, at least the following steps:
a) Sampling of electrochemical signals and/or impedances
b) Detection and/or classification of states of the sensor element regarding the humidification state of a sensor element or individual sensors of the humidification element on the basis of the determined electrochemical signals and/or impedances
c) Evaluation of amplitudes and changes in electrochemical signals and/or impedances to analyze saliva in terms of patient health status.

The wetting state can indicate completely or partially (insufficiently) moistened. However, other states such as the presence of toothpaste and the concentration of saliva in water can also be indicated. This makes it possible to determine the concentration of saliva and compensate for interfering factors such as toothpaste when measuring and evaluating the health status.

One way to detect the aforementioned conditions is to detect signal changes, time constants of exponential factors and/or signal variance calculation (ripple monitoring).

During the evaluation of amplitudes in step c), a signal decomposition of the raw signals or electrochemical signals can advantageously be carried out to analyze the useful component of the respective signal and/or to compensate for interference components.

The decomposition can be carried out using exponential models, which can be, for example, exponential decays or exponential process, or first order exponential step responses, especially of the $1-\exp(-t)$ type.

Another form of decomposition can be carried out by classifying signals and signal changes based on temporal patterns (signal processing in the time domain) or even features in the frequency domain.

Furthermore, a decomposition by classification of signals based on the course of derivatives of signals and/or as rate-of-change and/or as one or more approximate derivatives or approximate derivatives can be carried out.

After decomposition of signals into different components (signal decomposition), derivation of signal features/characteristics based on this decomposition can then be used to improve estimates of concentrations and/or to derive more accurate calibration curves.

The separation of different interference components from the useful part of the electrochemical signal or the impedance, i.e., the reaction part of the corresponding electrochemical reaction, can alternatively or advantageously be carried out by means of the Cottrel equation or other similar models of a physical and/or mathematical nature. The useful signal is then of interest for determining the concentration of indicators, in particular biomarkers, which individually or possibly together with other measured values can provide information about the state of health of the toothbrush user. The biomarkers can be detected by specific biosensors.

The method may further comprise a sampling of electrochemical signals after conditioning and/or stabilization of the sensor unit in a provided reference solution. This sampling can preferably take place after step c), e.g., when the toothbrush is put into operation for the first time, or before step a).

The sampling of signals after conditioning and/or stabilization has occurred can advantageously be initiated or detected in combination by a trigger or sensor, preferably a sensor for conductivity or impedance measurement, which detects the presence of the reference solution and/or saliva and/or indicates the end of a conditioning period. The trigger can preferably make the measurement based on the detected state or state transition.

Further, in particular following step c), one or more repetitions of measurements may be made to combine the information from multiple measurements, preferably to improve precision, improve the signal-to-noise (S/N signal-to-noise) ratio toward the signal, and/or compensate for interference.

Sampling of electrochemical signals, especially amperometric signals at different potentials can be carried out over several seconds or minutes.

The detection and classification of "dry" vs. "aerated after humidification" vs. "fully humidified" states and the associated transitions can be performed as described above.

This detection advantageously allows an assessment of the reliability of the measurements made by the biosensor and the other sensors and the health status determined from them.

The evaluation of the decay of electrochemical signals or impedances allows conclusions to be drawn about redox reactions and capacitive transients within the oral cavity.

The toothbrush, in particular the sensor arrangement, can have a temperature sensor as described previously. The temperature measurement can be carried out in an averaged manner over several days to obtain a reference of the body temperature. Furthermore, a sudden increase in temperature, e.g., in the case of a fever, can be detected, as well as a temperature increase that also advantageously increases gradually and/or recurs periodically. This can be advantageous e.g., for the determination of the fertility cycle, e.g., as part of a health monitoring or in addition thereto.

Optionally or additionally, the toothbrush may have a dispensing device for dispensing substances for treating diseases, particularly in the oral cavity, and/or for stimulating the immune system.

These can be specially prescribed by a doctor, with the toothbrush serving as a dosage device. Particularly in the case of diseases in the oral region, such as inflammation of the gums, the toothbrush can be used to apply a corresponding drug in a precise location and in conjunction with a mechanical-assistive massage during dosage by the bristles, e.g., on the gums. The dosage or the extent of the drug delivery can be carried out by the doctor or the patient at the toothbrush. In the case of the physician, the physician may have special access authorization for corresponding subprograms, e.g., via a Bluetooth transponder or code or the like, which prevents access to physician-specific subprograms of the toothbrush. Alternatively, or additionally, a program or a program setting for dosing can also be transferred to the toothbrush or the exchange station by remote access or via a data storage device, e.g., USB stick.

Another option is to use a reference liquid for conditioning the sensors. Water, for example, with a defined ion content, can be used for this purpose. This reference liquid, also called conditioning liquid, resets the sensors of the sensor arrangement to an initial value.

In addition, one or more calibration liquids can be used with one or more conductivities defined differently from the reference liquid. Thus, after a certain period of time, the measurement accuracy can be checked by the calibration liquid(s) and readjusted if necessary.

The reference liquid and the at least one calibration liquid may be part of the analysis system according to the invention.

The sensor arrangement as well as the brush head can be interchangeable and formed as a disposable article. The sensor arrangement advantageously allows both detection of a state of health and monitoring thereof. In selected cases of a disease, the type of disease and/or its manifestation or intensity can also be determined.

Multidimensional biomarkers can be used. Ideally, the toothbrush should be handled in such a way that its signals are collected and/or recorded at least once a day The data can then be stored over several days, weeks months, etc. to identify long-term trends.

Although the invention has been illustrated and described in detail by way of preferred embodiments, the invention is not limited by the examples disclosed, and other variations can be derived from these by the person skilled in the art without leaving the scope of the invention. It is therefore clear that there is a plurality of possible variations. It is also clear that embodiments stated by way of example are only really examples that are not to be seen as limiting the scope, application possibilities or configuration of the invention in any way. In fact, the preceding description and the description of the figures enable the person skilled in the art to implement the exemplary embodiments in concrete manner, wherein, with the knowledge of the disclosed inventive concept, the person skilled in the art is able to undertake various changes, for example, with regard to the functioning or arrangement of individual elements stated in an exemplary embodiment without leaving the scope of the invention, which is defined by the claims and their legal equivalents, such as further explanations in the description.

LIST OF REFERENCE SIGNS

1 Brush head
2 Bristles

3 Sensor arrangement
3' Spent sensor arrangement
4 Second sensor unit
5 First sensor unit
6 Electrode
7 Electrode
8 Third sensor unit
9 Mechanical interface
10 Exchange station
11 Exchange chamber
12 Separating device
13 Film roll
14 Charging station
15 Readout and/or evaluation unit
16 Transmitting module
17 Reservoir
20 Toothbrush head
21 Insertion slot
22 Cover segment
23 Base body
24 Bristles
25 Brush neck attachment
26 End face
30 Brush head
31 Base body
32 Bristles
33 Support surface
34 Sensor receptacle
35 Sensor receptacle
36 Sensor receptacle
37 Edge
40 Toothbrush head
41 Base body
42 Sensor unit
43 Insertion slot
45 Openings
47 Cover segment
50 Brush head
51 Sensor unit
52 Projection
53 Sensor arrangement
54 Recess
55 Sensors
$l_b$ Bristle length
l Length of insertion slot
h Height of insertion slot
R Insertion direction
100 Toothbrush
101 Handle

The invention claimed is:

1. A brush head of a toothbrush, the brush head comprising:
a plurality of bristles arranged for cleaning teeth; and
a sensor arrangement comprising a first sensor unit, a second sensor unit, and a third sensor unit, wherein the first sensor unit is non-interchangeably arranged on the brush head and the second sensor unit is interchangeably arranged on the brush head, wherein the second sensor unit is configured to determine pH or temperature of saliva, and wherein the third sensor unit is a biosensor unit arranged in a replaceable manner on or in the brush head,
wherein the first sensor unit is configured to detect a wetting state of the second sensor unit, as well as detect presence of toothpaste and concentration of the saliva in water, by
performing an impedance measurement of the saliva with one or more frequencies or frequency bands.

2. The brush head of claim 1, wherein the first or second sensor unit is a thin-layer, a thin-film sensor arrangement, a sensor chip, or a printed film.

3. The brush head of claim 1, wherein the brush head comprises:
a one-, two-, or three-way sensor adapter configured to link the sensor arrangement to the brush head.

4. The brush head of claim 3, wherein the sensor adapter has an electrical interface having spherical, gold-plated contact elements arranged as a linear one-dimensional array or a two-dimensional matrix and which is sealed off from liquids, including saliva.

5. The brush head of claim 1, wherein the first sensor unit, the second sensor unit, or the sensor arrangement has a reservoir or a supply line configured to deliver functional molecules, including binding ligands, luminophores, or fluorophores.

6. The brush head of claim 1, wherein the third sensor unit is configured to determine at least one physical substance property.

7. The brush head of claim 1, wherein the third sensor unit is configured to determine a fertility cycle of a user of the brush head.

8. The brush head according to claim 1, wherein the biosensor is a lactate sensor, glucose sensor, IgA sensor, IgM sensor, IgG sensor, CRP sensor, IL-6 sensor, lysozyme sensor, Tnf-a sensor, alpha macroglobulin sensor and/or as a sensor for detecting metabolites, bacteria causing periodontitis, parodontitis and/or caries, *Prevotella intermedia, Porphyromonas gingivalis, Tannerella forsythia, Treponema denticola* and/or the Aggregatibacter *actinomycetemcomitans* associated with aggressive periodontitis or as a GABA sensor for determining a concentration of the aforementioned compounds.

9. The brush head of claim 1, wherein the second sensor unit is arranged in a form-fitting or force-fitting manner on at least one side of the brush head or in the brush head.

10. An electric toothbrush, comprising:
a brush head, which comprises
a plurality of bristles arranged for cleaning teeth; and
a sensor arrangement comprising a first sensor unit, a second sensor unit, and a third sensor unit, wherein the first sensor unit is non-interchangeably arranged on the brush head and the second sensor unit is interchangeably arranged on the brush head, wherein the second sensor unit is configured to determine pH or temperature of saliva, and wherein the third sensor unit is a biosensor unit arranged in a replaceable manner on or in the brush head,
wherein the first sensor unit is configured to detect a wetting state of the second sensor unit, as well as detect presence of toothpaste and concentration of the saliva in water, by
performing an impedance measurement of the saliva with one or more frequencies or frequency bands.

11. The toothbrush of claim 10, further comprising:
a handle; and
a mechanical interface configured to releasably connect the brush head to the handle.

12. The toothbrush of claim 11, further comprising:
a radio module configured to transmit data with an external device for data processing to determine a health condition; or
a module for inductive power transmission to the handle of the toothbrush.

13. The toothbrush of claim 10, further comprising:
a control or evaluation unit configured to acquire raw data during measurement of saliva by the second sensor unit at a sampling rate of 10-1000 Hz.

14. The toothbrush of claim 13, wherein the control or evaluation unit is configured to acquire the raw data during the measurement of the saliva by the second sensor unit in a measurement period of at least 3 to 500 seconds.

15. A method comprising:
providing an electric toothbrush comprising an external device and a brush head, wherein the brush head comprises a plurality of bristles arranged for cleaning teeth and a sensor arrangement comprising a first sensor unit, and a second sensor unit, and a third sensor unit, wherein the first sensor unit is non-interchangeably arranged on the brush head and the second sensor unit is interchangeably arranged on the brush head, wherein the second sensor unit is configured to determine pH or temperature of saliva, and wherein the third sensor unit is a biosensor unit arranged in a replaceable manner on or in the brush head, wherein the first sensor unit is configured to detect a wetting state of the second sensor unit, as well as detect presence of toothpaste and concentration of the saliva in water, by performing an impedance measurement of the saliva with one or more frequencies or frequency bands;
receiving, by the external device from the electric toothbrush, raw signals, wherein the raw signals include raw signals from the first sensor unit for determining the wetting state of the second sensor unit, raw signals from the second sensor unit, and raw signals from the third sensor unit;
sampling, by the external device, the electrochemical signals with a predetermined sampling rate;
detecting and classifying, by the external device, states of the first sensor unit with respect to a wetting state of the second sensor unit based on sampled electrochemical signals; and
evaluating, by the external device, amplitudes, changes in the electrochemical signals, redox reactions, or capacitive transients in order to analyze saliva in terms of a user's state of health.

16. The method of claim 15, wherein the evaluation comprises a decomposition or filtering of the sampled electrochemical signals into a useful component and one or more interfering components, wherein the useful component represents a redox reaction component of the sampled electrochemical signals, which is for determining concentration determination of biomarkers.

17. The method of claim 16, wherein after the evaluation or before the sampling, the method further comprises:
sampling of the electrochemical signals after conditioning or stabilization in a provided reference solution;
repeating measurements to combine information from multiple measurements, to improve precision of the measurement, a signal-to-noise ratio, or to compensate for interference with the useful component.

18. The method of claim 15, wherein the user's state of health comprises medication intake by the user.

19. The method of claim 15, wherein the user's state of health comprises a concentration of viruses in the user's body, bacteria in the user's body, an inflammatory status of the body, a risk of diabetes or cardiovascular disease of the user's body, or a fertility cycle of the user.

* * * * *